United States Patent [19]

Malick

[11] 4,015,296
[45] Apr. 5, 1977

[54] ELASTIC STOCKING

[76] Inventor: Frank Malick, 8836 Major Ave., Morton Grove, Ill. 60053

[22] Filed: Mar. 17, 1976

[21] Appl. No.: 667,709

[52] U.S. Cl. .............................. 2/239; 24/201 B; 24/205.15 H; 223/111
[51] Int. Cl.² ...................................... A41B 11/00
[58] Field of Search .............................. 2/239, 240; 24/205.15 H, 205.15 R, 201 B, 205 B; 223/111; 46/239, 240

[56] References Cited

UNITED STATES PATENTS

| | | | |
|---|---|---|---|
| 1,775,714 | 9/1930 | Bass | 2/239 X |
| 2,287,878 | 6/1942 | Hard | 24/205 B |
| 2,513,639 | 7/1950 | Goodman | 2/239 |
| 2,666,208 | 1/1954 | Funk | 2/239 X |
| 3,325,869 | 6/1967 | Younger | 24/201 B X |
| 3,471,151 | 10/1969 | Pfenninger | 46/239 X |
| 3,836,189 | 9/1974 | Borrelli | 24/205.15 H X |
| 3,907,181 | 9/1975 | Thomas | 223/111 |

Primary Examiner—H. Hampton Hunter
Attorney, Agent, or Firm—Erwin S. Teltscher

[57] ABSTRACT

An elastic stocking has external and internal sides; a leg engaging portion thereof includes two longitudinal edges, and each of the edges has internal and external sides, respectively. The stocking includes a zipper which has two synthetic plastic material engaging portions and magnetic material closing means. The latter is movable along the engaging portions for closing and opening the zipper. The engaging portions are attached to the internal sides of the longitudinal edges, respectively. Upon the closing means having attached the engaging portions to one another, the longitudinal edges overlap with one another and substantially prevent the zipper being visible from the external side of the stocking.

2 Claims, 2 Drawing Figures

ELASTIC STOCKING

BACKGROUND OF THE INVENTION

1. Field of the Invention

The field of the invention relates to an elastic stocking.

2. Description of the Prior Art

Elastic stockings are known which serve to either support an infirm or weak leg, or are used as a cover for an artificial leg. The known stockings of the above type are either unitary in construction, or are provided in several separate portions, such as a leg portion and a foot engaging portion. A unitary stocking has the disadvantage of being difficult to put on, while a stocking having a plurality of portions is inconvenient, since the various portions thereof could be mixed up or lost during cleaning or storing.

SUMMARY OF THE INVENTION

It is accordingly an object of the present invention to provide a stocking particularly for an artificial leg, which is provided with closing means which open and close the stocking for easy application to a leg or artificial leg of a wearer and easy removal therefrom, while having substantially the appearance of a unitary stocking.

I accordingly provide an elastic stocking which has external and internal sides and which has a leg engaging portion, wherein the leg engaging portion has internal and external sides. The elastic stocking includes a zipper which has two synthetic plastic material engaging portions and a magnetic material closing means which is movable along the engaging portions for closing and opening of the zipper. The engaging portions are attached to the internal sides of the longitudinal edges, respectively. Upon the closing means having attached the engaging portions to one another, the longitudinal edges overlap with one another and thereby substantially prevent the zipper from being visible from the external side of the stocking.

A magnet means for moving the magnetic material closing means on the external side of the stocking along the edges permits easy closing and opening of the zipper in a contactless manner. The elastic stocking is preferably made of flesh-colored rubber.

BRIEF DESCRIPTION OF THE DRAWING

The present invention will be better understood with reference to the accompanying drawing, in which.

DESCRIPTION OF THE PREFERRED EMBODIMENT

Figures 1, 2:
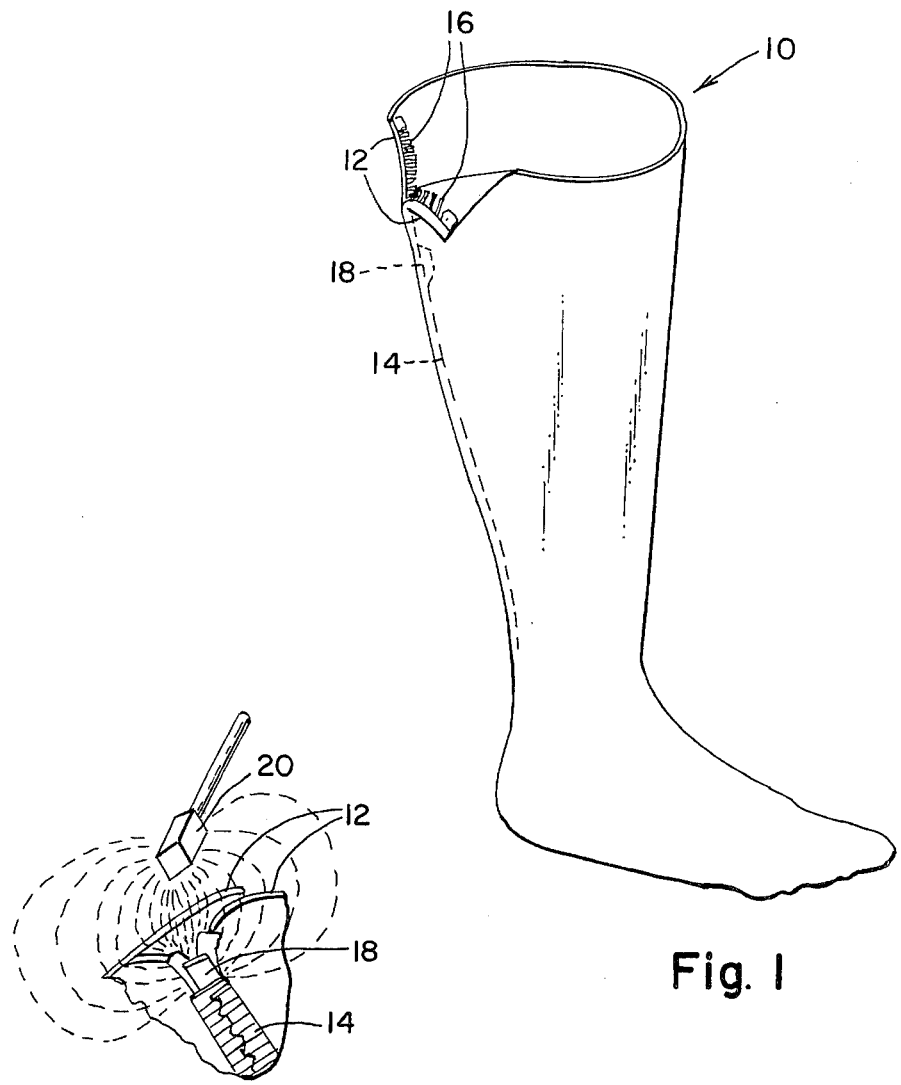
FIG. 1 shows a perspective view of the elastic stocking, according to the present invention.
FIG. 2 shows a detail of the zipper of the stocking and the magnetic closing means.

The drawing shows an elastic stocking 10 having external and internal sides, and a leg engaging portion which includes two longitudinal edges 12, wherein each of the edges 12 has internal and external sides. A zipper 14 which has two synthetic plastic material engaging portions 16 and magnetic material closing means 18 movable along the engaging portions for closing and opening the zipper, has its engaging portions attached to the internal sides of the longitudinal edges respectively. Upon the closing means 18 having attached the engaging portions 16 to another, the longitudinal edges 12 overlap with one another and thereby substantially prevent the zipper 14 from being visible from the external side of the stocking 10. Magnet means 20 are preferably provided for moving the magnetic material closing means 18 on the external side of the stocking 10 along the edges 12 for contactless closing and opening of the zipper 14. The elastic stocking 10 is preferably made of flesh-colored rubber.

Although the invention has been described with respect to a preferred form thereof, it is to be understood that it is not to be so limited since changes can be made therein which are within the full intended scope of this invention as defined by the appended claims.

What is claimed is:

1. An elastic stocking having external and internal sides, and a leg engaging portion including two longitudinal edges having internal and external sides, respectively, comprising:

a zipper having two synthetic plastic material engaging portions and magnetizable material slider means movable along said engaging portions from a first position to a second position and vice versa for closing and opening said zipper, respectively, said engaging portions being attached to said internal sides of said stocking and spaced from said longitudinal edges, whereby said edges overlap in the closed portion;

magnet means for moving said magnetizable material slider means, said magnet means being positioned on the external side of said stocking along said edges for selectively closing and opening said zipper contactlessly, whereby, upon said slider means having attached said engaging portions to one another in said first position and upon said magnet means moving said slider means from said first to said second position, said longitudinal edges overlap with one another thereby substantially preventing said zipper being visible from the external side of said stocking.

2. An elastic stocking according to claim 1 made of flesh-colored rubber.

* * * * *